US011213263B2

(12) United States Patent
Agrahari et al.

(10) Patent No.: US 11,213,263 B2
(45) Date of Patent: Jan. 4, 2022

(54) SYSTEM AND METHOD FOR POSITIONING A MOBILE MEDICAL IMAGING SYSTEM

(71) Applicant: KONINKLIJKE PHILIPS N.V., Eindhoven (NL)

(72) Inventors: Shailesh Kumar Agrahari, Pune (IN); Ravindra Bhat, Eindhoven (NL); Amit Agrahari, Pune (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 42 days.

(21) Appl. No.: 16/649,701

(22) PCT Filed: Sep. 25, 2018

(86) PCT No.: PCT/EP2018/075912
§ 371 (c)(1),
(2) Date: Mar. 23, 2020

(87) PCT Pub. No.: WO2019/063525
PCT Pub. Date: Apr. 4, 2019

(65) Prior Publication Data
US 2020/0253570 A1 Aug. 13, 2020

(30) Foreign Application Priority Data

Sep. 27, 2017 (EP) ..................................... 17193396

(51) Int. Cl.
*A61B 6/00* (2006.01)
*A61B 6/10* (2006.01)
(52) U.S. Cl.
CPC ............ *A61B 6/4405* (2013.01); *A61B 6/102* (2013.01); *A61B 6/4441* (2013.01); *A61B 6/547* (2013.01)

(58) Field of Classification Search
CPC ... A61B 6/4405; A61B 6/4275; A61B 6/4441; A61B 6/547
See application file for complete search history.

(56) References Cited

U.S. PATENT DOCUMENTS 5,695,500 A 12/1997 Taylor et al.
7,065,393 B2 6/2006 Sati et al.
(Continued)

OTHER PUBLICATIONS

PCT/EP2018/075923 ISR & WO, Nov. 23, 2018, 13 Page Document.

(Continued)

*Primary Examiner* — Dani Fox (57) ABSTRACT

The present invention relates to mobile imaging. In order to provide a mobile medical imaging system (100) with improved positioning characteristics, A positioning arrangement (126) is provided. The positioning arrangement comprises at least one positioning sensor (128). The at least one positioning sensor determines a current distance between a mobile structure of a mobile medical imaging system and at least one object in an environment of the mobile medical imaging system. The at least one positioning sensor operates in a first mode if a current distance is greater than a predetermined threshold, and/or in a second mode, if the current distance is smaller than the predetermined threshold. In the first mode, the at least one positioning sensor operates at a first spatial resolution, and, in the second mode, the at least one positioning sensor operates at a second spatial resolution, which second spatial resolution differs from the first spatial resolution.

11 Claims, 5 Drawing Sheets

(56) References Cited

U.S. PATENT DOCUMENTS

| | | |
|---|---|---|
| 9,144,145 B2 * | 9/2015 | Furst .................... A61B 6/4452 |
| 2002/0174515 A1 * | 11/2002 | Strong ................ B60B 33/0015 16/110.1 |
| 2004/0015077 A1 | 1/2004 | Sati et al. |
| 2005/0001862 A1 | 1/2005 | Tesar et al. |
| 2006/0078091 A1 | 4/2006 | Lasiuk et al. |
| 2008/0031413 A1 | 2/2008 | Bouvier et al. |
| 2011/0002556 A1 | 2/2011 | Hol et al. |
| 2014/0163736 A1 | 6/2014 | Azizian et al. |
| 2016/0296185 A1 | 10/2016 | Gemmel |
| 2017/0014203 A1 | 1/2017 | De Mathelin et al. |

OTHER PUBLICATIONS

Gustafsson et al: "Positioning Using Time-Difference of Arrival Measurements"; IEEE 2003, ICASSP, VI-553-VI-556.
Licznerski et al: "Ultrasonic System for Accurate Distance Measurement in the Air" Ultrasonics 51 (2011), pp. 960-965.
Mahfouz et al: "Investigation of High-Accuracy Indoor-3-D Positioning Using UW Technology"; IEEE Transactions on Microwave Theory and Techniques, vol. 56, No. 6, Jun. 2008, pp. 1316-1330.
Shen et al: "Performance Comparison of TOA and TDOA Based Location Estimation Algorithms in LOS Environment"; Proceedings of the 5th Workshop on Positioning, Navigation and Communication 2008 (WPNC'08). pp. 71-78.

* cited by examiner

SYSTEM AND METHOD FOR POSITIONING A MOBILE MEDICAL IMAGING SYSTEM

CROSS-REFERENCE TO PRIOR APPLICATIONS

This application is the U.S. National Phase application under 35 U.S.C. § 371 of International Application No. PCT/EP2018/075912, filed on Sep. 25, 2018, which claims the benefit of European Patent Application No. 17193396.3, filed on Sep. 27, 2017. These applications are hereby incorporated by reference herein.

FIELD OF THE INVENTION

The invention generally relates to positioning of a mobile medical imaging system relative to an object, and more specifically to a positioning arrangement for a mobile medical imaging system, to a mobile medical imaging system and to a method for positioning a mobile medical imaging system.

BACKGROUND OF THE INVENTION

In healthcare, mobile systems, such as C-arm stands, are used to move imaging sensors, such as X-ray systems, for example, to a desired position. In an example, such mobile systems are aligned manually. Thus, a surgeon needs to align a mobile system in a trial and error procedure. This means, the surgeon has to re-position a mobile system after movement by using multiple X-ray exposure and by comparing measurements determined at a current position and at a target position. This method is a manual iterative process and, therefore, very time consuming.

Document U.S. Pat. No. 7,065,393 B2 shows a system that includes a module for determining positions of an imaging source and an imaging receptor and a local gravity vector to determine an imaging source focal point displacement. A problem exists when an overlay of, for example pre-op CT/MR images and a live 2D fluoro image is needed. Such an overlay is not possible with a system based on a manual alignment of a mobile system, since a manual alignment results in measurements with a high variance. Thus, a manual alignment is not precise enough for such an overlay.

SUMMARY OF THE INVENTION

Hence, it would be desirable to provide improved and accurate positioning of a mobile medical imaging system.

This is solved by the subject-matter of the independent claims; further embodiments are incorporated in the dependent claims. It should be noted that the following described aspects of the invention apply also for the positioning arrangement for a mobile medical imaging system, for a mobile medical imaging system and for a method for positioning a mobile medical imaging system.

In a first aspect, a positioning arrangement for a mobile medical imaging system is provided. The positioning arrangement includes at least one first positioning sensor configured to operate at a first spatial resolution and capable of non-line of sight operation, at least one second positioning sensor configured to operate at a second spatial resolution that is higher than the first spatial resolution, and a processor.

The processor may be configured to determine a current distance between a mobile structure of a mobile medical imaging system and at least one object in an environment of the mobile medical imaging system. In particular, in a first mode, if the current distance is greater than a predetermined threshold, the processor is configured to use at least one first positioning sensor. That is, positioning information or signals from the at least one first positioning sensor is received by the processor and used in determining the current distance. Further, in a second mode, if the current distance is smaller than the predetermined threshold, the at least one second positioning sensor is used in determining the current position.

In particular, it is provided that the positioning arrangement can operate in the first mode or in the second mode as alternating modes. For example, the positioning arrangement may operate in the first mode or in the second mode dependent on a current distance between a mobile structure and an extenral object being larger or smaller than a predetermined threshold.

In a second aspect, a mobile medical imaging system is provided. The mobile medical imaging system includes a mobile structure for holding an imaging device and a positioning arrangement according to the example described above. The at least one positioning sensor determines a current distance between the mobile structure of the mobile medical imaging system and at least one object in an environment.

The imaging device may be a fluoro image system and may comprise an X-ray source and a detector. The detector and the X-ray source may be mounted to the mobile structure, particularly opposite each other. Alternatively, either the X-ray source or the detector may be mounted to the mobile structure, so that the detector or the X-ray source which is not mounted to the mobile structure may be moved independent from the mobile structure.

The mobile structure may comprise an arc, such as a C-arm for holding and moving the medical imaging system.

The C-arm may be configured for horizontal and angular movement of the medical imaging system, preferably with eight degrees of freedom.

In an example, the mobile structure comprises a C-ram with an X-ray source mounted to a first end of the C-arm and a detector mounted to a second end of the C-arm.

In an embodiment, the predetermined threshold may be between 10 cm and 500 cm, preferably between 40 cm and 200 cm, more preferably between 100 cm and 140 cm, most preferably 125 cm.

The positioning arrangement comprises at least one first positioning sensor, at least one second positioning sensor and a processor. The positioning arrangement may determine a current position of the mobile medical imaging system using the at least one first positioning sensor in the first mode. Further, the positioning arrangement may determine a current position of the mobile medical imaging system using the at least one second positioning sensor in the second mode. The at least one first positioning sensor may be an ultrawideband sensor, such as an ultrawideband radar sensor, for example, and the at least one second positioning sensor may be an ultrasound sensor, for example. The output of the second sensor may be in form of an analog envelop signal.

Thus, in the first mode, for a system-to-object distance above the threshold, the positioning arrangement may operate using the first positioning sensor, and in the second mode, for a system-to-object distance below the threshold, the positioning arrangement may operate using the second positioning sensor. For example, if the system is at a relatively high distance to any object, a relatively rough positioning is carried out using an ultrawideband sensor, and the positioning arrangement switches to a second mode involving finer positioning using an ultrasound sensor once a system-to-object distance is reduced below a predetermined threshold.

In an embodiment, the positioning arrangement is configured to detect an obstacle between a current position of the mobile medical imaging system and the at least one object.

For example, the positioning system may comprise at least a first pair of transmitter-receiver sensors and a second pair of transmitter-receiver sensors, and the processor may be configured to output a warning for an obstacle using a user interface, if a differential value of a measurement determined by the at least one first pair of transmitter-receiver sensors and an expected measurement calculated based on a measurement of the second pair of transmitter-receiver sensors is greater than a given security threshold.

For example, the mobile medical positioning system comprises an output device, a memory and a processor, wherein the processor is configured to determine a position and/or orientation of the mobile medical imaging system at a first instant, and to store the position and/or orientation determined at the first instant in the memory, and to output instructions for moving the mobile medical imaging system to the position and/or orientation stored in the memory via the output device at a second instant.

Preferably, the at least one positioning sensor may be attached to a C-stand of a mobile imaging device. More preferably, a transmitter or a receiver of the at least one positioning sensor may be attached to a mobile imaging device and a corresponding receiver or transmitter may be attached to a reference point, such as an object in an environment of the mobile imaging device, for example.

In a third aspect, a method for positioning a mobile medical imaging system is provided. The method includes a first step of determining a current distance between the medical imaging system and at least one object in an environment of the mobile medical imaging system by using a positioning arrangement comprising at least one first and at least one second positioning sensor. The method further includes a second step of operating the at least one first positioning sensor in a first mode at a first spatial resolution, if the current distance between the mobile medical imaging system and the at least one object is greater than a predetermined threshold. The method further includes a third step of operating the at least one second positioning sensor in a second mode at a second spatial resolution, which differs from the first spatial resolution, if the current distance between the mobile medical imaging system and the at least one object is smaller than the predetermined threshold.

In an example, the positioning arrangement comprises at least one positioning sensor. The at least one positioning sensor determines a current distance between a mobile structure of a mobile medical imaging system and at least one object in an environment of the mobile medical imaging system. Further, the positioning arrangement is configured to determine a current position of the mobile medical imaging system based on signals determined by the at least one positioning sensor in a first mode, if a current distance is greater than a predetermined threshold and to determine a current position of the mobile medical imaging system based on signals determined by the at least one positioning sensor in a second mode, if the current distance is smaller than the predetermined threshold. In the first mode, the at least one positioning sensor operates at a first spatial resolution. In the second mode, the at least one positioning sensor operates at a second spatial resolution, which second spatial resolution differs from the first spatial resolution. The at least one positioning sensor is configured to operate in the first mode and the second mode simultaneously or the at least one positioning sensor is configured to operate in the first mode and the second mode in an alternating manner.

The second and third step may be arranged as simultaneous steps or as alternating steps. This means the at least one positioning sensor can be operated in the first mode and switched to the second mode, if the current distance between the mobile medical imaging system and the at least one object becomes smaller that the predetermined threshold. Alternatively, the at least one sensor can be run in the first mode and in the second mode simultaneously. If the at least one sensor is run in the first mode and in the second mode simultaneously, either a signal determined in the first mode or a signal determined in the second is used for positioning of the mobile medical imaging system.

According to an aspect, at least one positioning sensor is used that can be run in a first mode for coarse movement of a mobile medical imaging system using a first spatial resolution and in a second mode for fine movement of the mobile medical imaging system using a second spatial resolution that is higher, i.e. that creates more datapoints per distance than the first resolution. Switching between the first mode and the second mode is performed automatically depending on a current distance between the mobile medical imaging system and an object in an environment. Other devices, systems, and methods specifically configured to interface with such devices and/or implement such methods are also provided. Providing two different operating modes allows for coarse and fine positioning of the mobile medical imaging system and thus provides improved positioning of a mobile medical imaging system.

Additional aspects, features, and advantages of the present disclosure will become apparent from the following detailed description.

BRIEF DESCRIPTION OF THE DRAWINGS

Exemplary embodiments of the invention will be described in the following with reference to the following drawings.

DETAILED DESCRIPTION OF EMBODIMENTS

Figure 1:
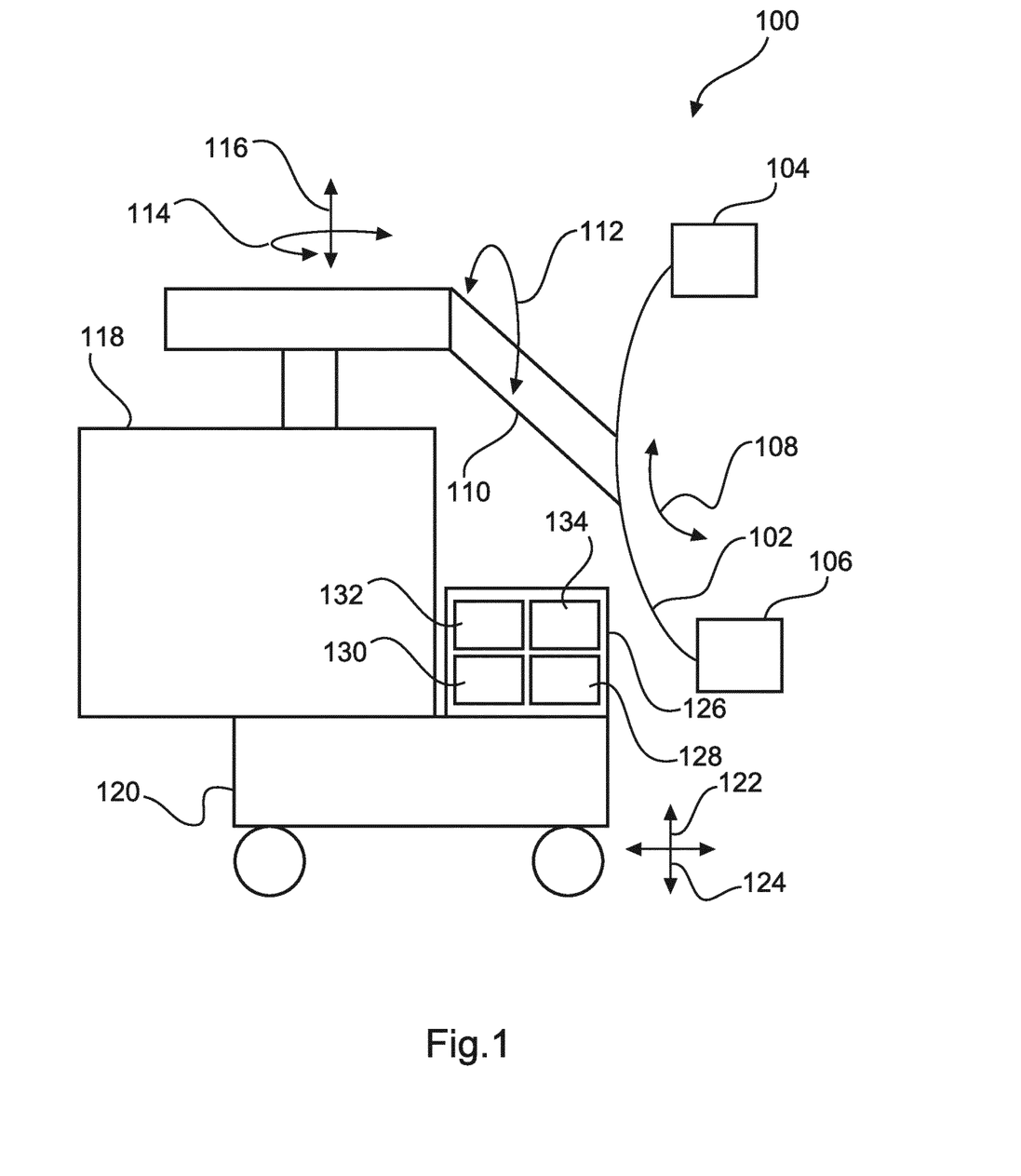
FIG. 1 shows a schematic drawing of an example of a mobile medical imaging system with an example of a positioning arrangement.

In FIG. 1, a mobile medical imaging system 100 is shown. The mobile medical imaging system 100 has a mobile structure 102 in form of a C-arm. Attached to the mobile structure 102 is an imaging device comprising an X-ray source 104 and a detector unit 106. The mobile medical imaging system 100 will also be described in more details below with reference to the further drawings.

The mobile structure 102 can be moved to change position, particularly an angle of the imaging device with respect to a reference point such as an operating table, as indicated by arrow 108. For horizontal and vertical movement, the mobile structure 102 is attached to a support member 110, which can be moved laterally, as indicated by arrow 112, in a vertical direction, as indicated by arrow 114 and in horizontal direction, as indicated by arrow 116. The support member 110 is connected to a base member 118 mounted to a mobility member 120, which can be moved laterally, as indicated by arrow 122 and horizontal, as indicated by arrow 124. Attached to the mobility member 120 is a positioning arrangement 126 that includes a positioning sensor 128 of a positioning arrangement. The positioning sensor 128 may be a transmitter or a receiver exchanging signals with a corresponding receiver or transmitter attached to a reference point, such as an object in an environment of the mobile medical imaging system 100.

In an example, the positioning arrangement 126 comprises an output device 130, a memory 132, and a processor 134. The processor 134 is configured to determine a position of the mobile medical imaging system 100 using the positioning sensor 128 at a first instant, to store the position determined at the first instant in the memory 132 and to output instructions for moving the mobile structure 102 to the position stored in the memory 132 via the output device 130 at a second instant.

In an example, the positioning arrangement may be provided as a kit to upgrade an existing mobile imaging system, e.g. to achieve a system as described above.

Figure 2:
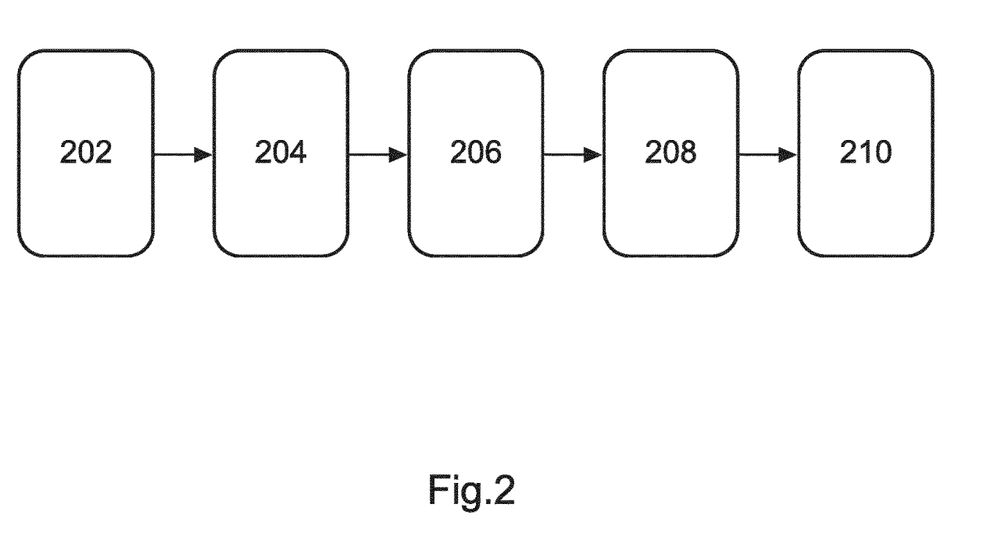
FIG. 2 shows an example of a schematic flowchart for calculation of a current position of a mobile medical imaging system, according to an embodiment.

Turning now to FIG. 2, a method for calculation of a current position of a mobile medical imaging system, according to an embodiment is shown. Therein, in detection step 202, a signal is detected by a positioning sensor of the mobile medical imaging system. The signal detected in the detection step 202 is processed in processing step 204 by applying filters, such as bandpass filter, for example. Based on the signal filtered in the processing step 204, a relative time stamping to distance conversion is performed in conversion step 206. The output of the conversion step 206 is used for calculation of an exact distance of the sensor to a particular object sensed by the sensor using a time-difference-of-arrival and/or a time-of-flight algorithm in sensing step 208. The exact distance calculated in the sensing step 208 is used as input for a hybrid positioning module 210 that switches at least one sensor of a positioning arrangement of the mobile medical imaging system between a first mode and a second mode and triggers the at least one sensor respectively.

Figure 3:
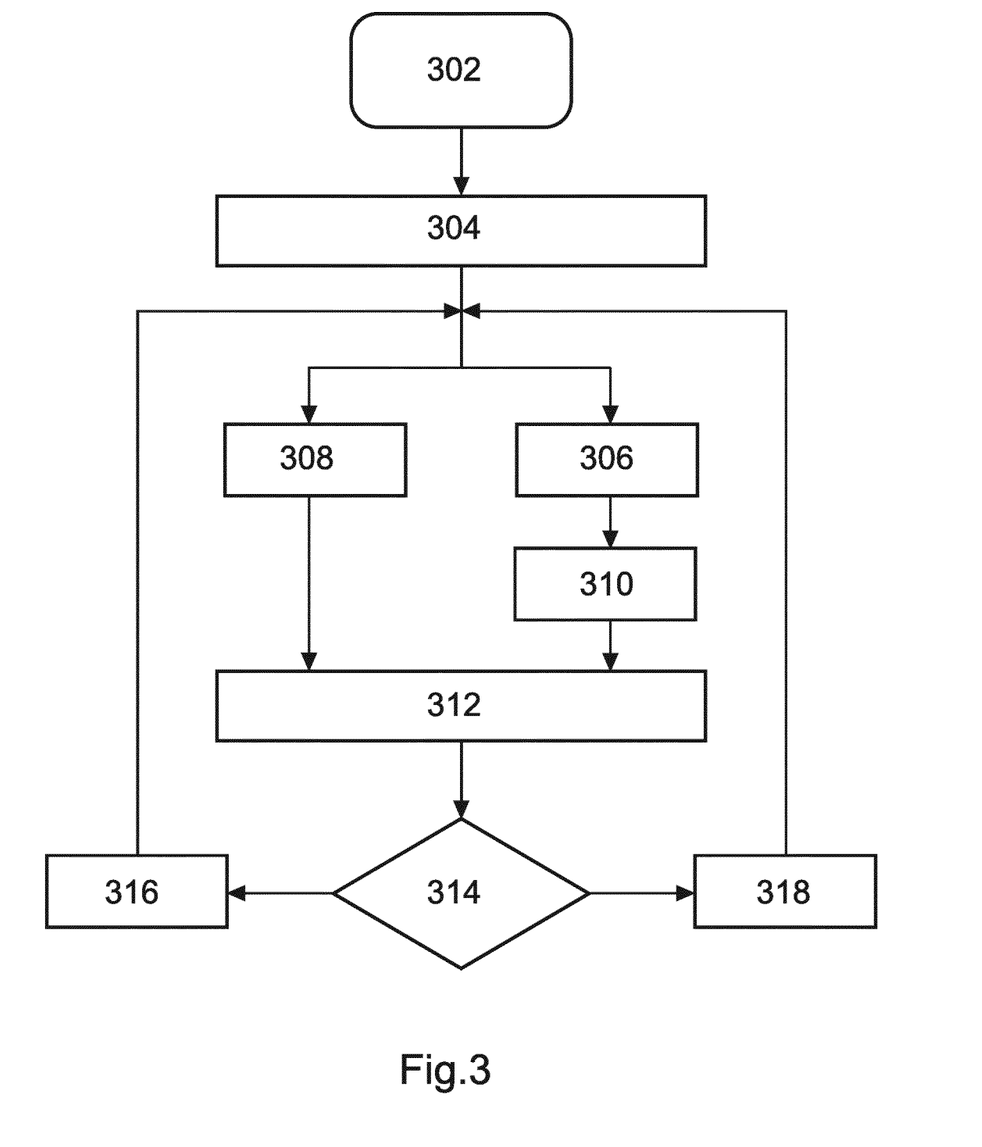
FIG. 3 shows an example of a schematic flowchart for operating a two-sensor system for positioning a mobile medical imaging system.

Turning now to FIG. 3, a method for precise positioning of a mobile medical imaging system comprising two sensor modules, according to an embodiment, is shown. First, the system is started in starting step 302. In an initializing step 304, a first positioning sensor and a second positioning sensor are initialized.

In a first determination step 306, a distance between the mobile positioning system and an object is determined using the first positioning sensor. The first positioning sensor is an ultrawideband sensor capable of sensing information in a non-line of sight environment.

In a second determination step 308, a distance between the mobile positioning system and the object is determined using the second positioning sensor. The second positioning sensor is an ultrasound sensor.

Based on particular measurements of sensor units of the first positioning sensor, an obstacle detection algorithm is performed in detection step 310. Therefore, particular measurements of the sensor units, i.e. measurements determined by particular transmitter-receiver pairs, are compared. If a differential value between a measurement determined by at least one sensor unit and a measurement determined by the remaining sensor units is greater than a given security threshold, an obstacle warning is shown in a user interface, for example.

In a calculation step 312, if no obstacle warning is to be shown, a distance between the mobile medical imaging system and at least one object in the environment, such as an operating table, for example, is calculated based on the measurements determined in the first determination step 306 and/or the second determination step 308.

In switching step 314, the distance calculated in the calculation step 312 is compared with a predetermined threshold of 125 cm, for example. The outcome of this comparison is used to decide, whether the further positioning of the mobile medical imaging system is to be performed in a first mode 316 or in a second mode 318. Since in the first mode 316 a first spatial resolution is used that is preferably smaller than a second spatial resolution used in the second mode 318, the first mode 316 is used for coarse positioning of the mobile medical imaging system and the second mode 318 is used for fine positioning of the mobile medical imaging system.

Thus, if the distance determined in the calculation step 312 is greater than the predetermined threshold, a positioning arrangement of the mobile medical imaging system is used in the first mode 316 with a first spatial resolution of one datapoint per 10 cm, for example. Respectively, further measurements for positioning the mobile medical imaging system are determined using the first positioning sensor in the first mode 316. However, if the distance determined in the calculation step 312 is smaller than the predetermined threshold, the positioning arrangement of the mobile medical imaging system is switched to the second mode 318 with a second spatial resolution of one datapoint per 5 mm, for example. Thus, further measurements for positioning the mobile medical imaging system are determined using the second positioning sensor in the second mode 318.

Since the second spatial resolution used in the second mode 318 is higher than the first spatial resolution used in the first mode 316, which means that the positioning arrangement determines more data points per distance and/or time in the second mode 318 than in the first mode 316, the mobile medical imaging system can be moved much more precisely in the second mode 318 than in the first mode 316.

As the first spatial resolution used in the first mode 316 is smaller than the second spatial resolution used in the second mode 318 and the first positioning sensor preferably is a sensor that works in a non-sight environment, the mobile medical imaging system can be moved very quick, i.e. with higher speed in the first mode 316 than in the second mode 318. In combination with the obstacle detection algorithm performed in the detection step 310 an operator can move the mobile medical imaging system with high speed even in a non-sight environment.

The measurements determined in the first mode 316 or in the second mode 318 are used to calculate guiding instructions that are shown on a user interface, for example. Thus, the operator can maneuver the mobile medical imaging system according to the guiding instructions shown on the user interface with high speed, if the positioning system is run in the first mode 316. Alternatively, the operator can maneuver the mobile medical imaging system very precisely, if the positioning system is run in the second mode 318. Since the switching between the first mode 316 and the second mode 318 is performed automatically using the system disclosed herein, the operator who maneuvers the mobile medical imaging system can move the mobile medical imaging system with high speed towards a design space, such as a coordinate system around an operating table and move the mobile medical imaging system precisely within the design space.

Figure 4:
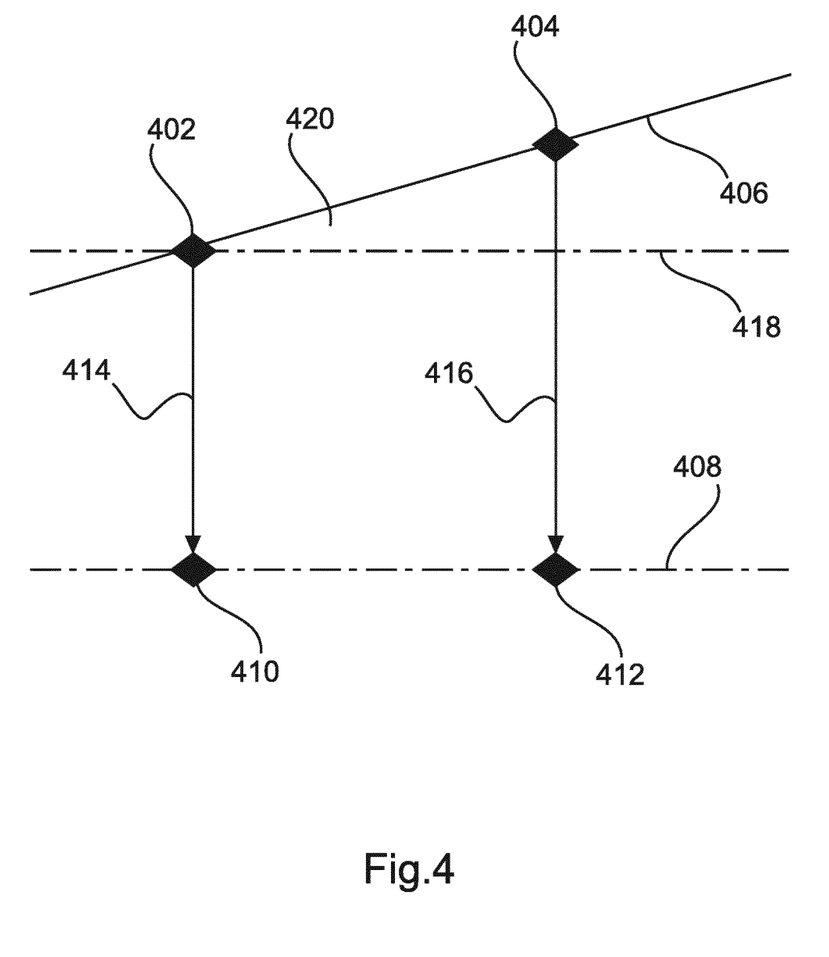
FIG. 4 shows a schematic illustration of a measurement of an angular orientation of a mobile medical imaging system based on multiple sensors, according to an embodiment.

In FIG. 4, an angular measurement is shown using a first transmitter 402 and a second transmitter 404 attached to a mobile medical imaging system 406. A dashed line 408 shows an alignment of a reference point, such as an operating table, for example. A first receiver 410 and a second receiver 412 are attached on the operating table. Since a first distance 414 between the first transmitter 402 and the first receiver 410 is smaller than a second distance 416 between the second transmitter 404 and the second receiver 412, the operating table must be in an angular alignment with the mobile medical imaging system 406. By using a reference position of the mobile medical imaging system, which is parallel to the operating table as shown by dashed line 418, an angle 420 between the mobile medical imaging system 406 and the operating table can be calculated.

As mentioned, the mobile medical imaging system comprises a mobile structure, such as a C-arm equipped with an X-ray imaging device. The medical imaging system can be an interventional X-ray image system for use in a catheterization laboratory (cathlab), for example.

During an operation or intervention, an imaging device is moved several times. In a common system, the imaging device has to be re-positioned in a manual time consuming and iterative process involving try and error imaging after each movement. Therefore, a mobile structure that holds the imaging device is moved relative a patient's body and X-ray exposers are used to locate a current position of the imaging device relative to a position of the imaging device before it was moved.

Thus, using a common system, the patient's body is exposed to several radiation exposures that may be avoided using the mobile medical imaging system disclosed herein.

As an effect, it is achieved to align, i.e. to position, an imaging device exact at a predetermined position, particularly without any need for radiation exposers. The mobile medical imaging system disclosed herein can be positioned precise and fast using the positioning arrangement disclosed herein. Further, the mobile medical imaging system may present a warning, if an obstacle is recognized in a trajectory planned for a movement of the mobile medical imaging system.

The mobile medical imaging system disclosed herein comprises a mobile structure for holding an imaging device and a positioning arrangement. The positioning arrangement comprises at least one positioning sensor that determines a current distance between a mobile structure of the mobile medical imaging system and at least one object in an environment of the mobile medical imaging system. The at least one positioning sensor is configured to operate in a first mode, if the current distance between the mobile medical imaging system and the at least one object is greater than a predetermined threshold, and to operate in a second mode, if the current distance between the mobile medical imaging system and the at least one object is smaller than the predetermined threshold.

Thus, the mobile medical imaging system disclosed herein is based on a positioning arrangement with a hybrid sensor mechanism that makes use of a current distance to at least one reference point, such as an operating table or any other reference point, to switch the positioning system between a first and a second mode. The current distance to the at least one reference point is preferably determined using the at least one sensor of the positioning arrangement.

If the current distance to a particular reference point is greater than a predetermined threshold, the positioning arrangement is operated in the first mode with a first spatial resolution.

If the current distance between to a particular reference point is smaller than a predetermined threshold, the positioning arrangement is operated in the second mode with a second spatial resolution.

Preferably, the positioning arrangement is operated in the first mode for coarse positioning and in the second mode for fine positioning.

For example, the positioning arrangement may be a hybrid sensor system comprising a first sensor that is used in the first mode and a second sensor that is used in the second mode. Thus, the first positioning sensor is used for positioning the mobile medical imaging system, particularly a mobile structure of the mobile medical imaging system, in a coarse way and also detect obstacles. This means the first sensor is used with low accuracy, i.e. with a small spatial resolution that creates a smaller number of datapoints per distance compared to a high resolution that is used in the second mode.

The first mode and the first sensor may be used to position the mobile structure towards a given design room.

The second sensor is used in the second mode for positioning the mobile medical imaging system, particularly a mobile structure of the mobile medical imaging system in a fine way. This means the second sensor is used with high accuracy, i.e. with a high spatial resolution that creates a higher number of datapoints per distance compared to the first sensor used for coarse positioning at a small spatial resolution, for example.

The second mode and the second sensor may be used to position the mobile structure within a given design room, such as a coordinate system, for example.

In general, the second spatial resolution used in the second mode is higher than the first spatial resolution used in the first mode and is based on a higher sampling rate, for example.

If a positioning system is used that comprises a first sensor and a second sensor, the first sensor may be a sensor module capable of non-line of sight operation, such as an ultrawideband sensor module. The second sensor may be an ultrasound sensor module. Each, the first sensor and the second sensor may be used as multiple receivers and single transmitter or single receiver and multiple transmitter configurations.

An obstacle detection mechanism may be implemented based on at least one sensor. Therefore, each transmitter-receiver pair of the at least one sensor performs a distance measurement. If an obstacle is present between one of the transmitter-receiver pair and a particular reference point, the particular transmitter-receiver pair will show a difference in distance with respect to other transmitter-receiver pairs. With help of this mechanism asymmetric variation can be eliminated.

The point at which the first positioning sensor is deactivated and the second positioning sensor is used, i.e. the point where the positioning sensor used for positioning the mobile medical imaging system is switched, may be a given distance between the mobile medical imaging system and the reference point of about 125 cm, for example. This means that an automatic switching and triggering procedure from the first positioning sensor to the second positioning sensor is performed, if the mobile medical imaging systems is moved closer than 125 cm to the reference point.

The invention disclosed herein is beneficial for a precise and fast positioning of a mobile medical imaging system. By using the systems and methods disclosed herein, an overlay or stitching of pictures can be achieved. Particularly, an overlay of pre-operation CT and/or MR image data with live 2D fluoro image data determined by the mobile medical imaging system can be achieved by using the systems and methods disclosed herein.

Further, by using an obstacle recognition method according to an embodiment of the mobile medical imaging system disclosed herein, a collision of the mobile medical imaging system with an obstacle can be avoided during movement of the mobile medical imaging system, even if a surgeon or an operator who is moving the mobile medical imaging system is not in a line of sight of a trajectory of the mobile medical imaging system.

Figure 5:
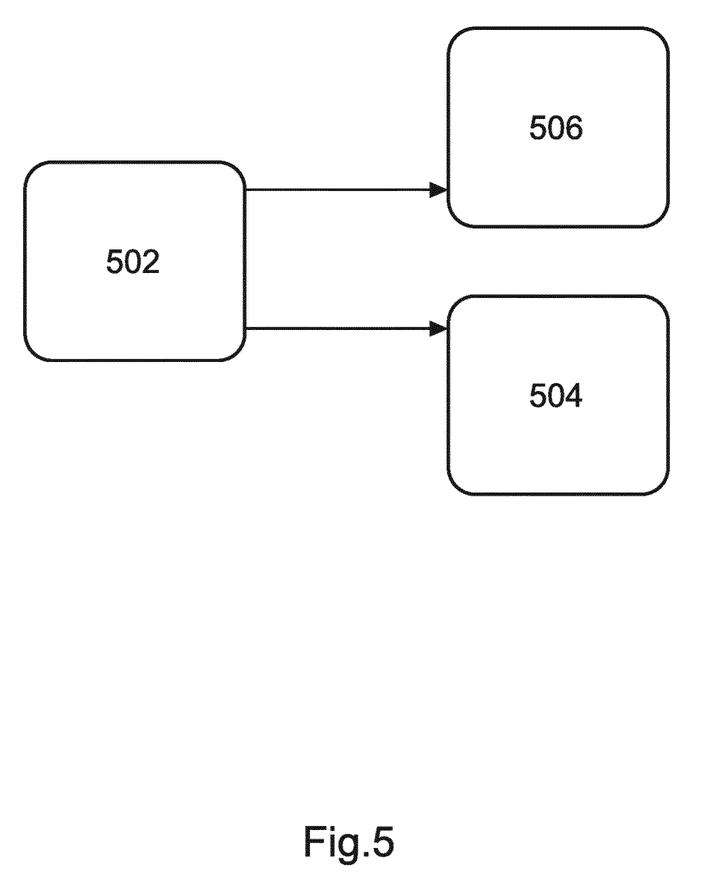
FIG. 5 shows a schematic illustration of a further example of a method for positioning a mobile medical imaging system.

FIG. 5 shows a schematic illustration of a method 500 for positioning a mobile medical imaging system. The method 500 comprises the following steps: In a first step 502, also referred to as step a), a current distance between a mobile structure and at least one object in an environment of the mobile medical imaging system is determined by using a positioning arrangement comprising at least one positioning sensor. In a second step 504, also referred to as step b1), a current position of the mobile medical imaging system is determined using signals determined by the at least one positioning sensor in a first mode at a first spatial resolution, if the current distance between the mobile medical imaging system and the at least one object is greater than a predetermined threshold. Or alternatively to the first step, in a third step 506, also referred to as step b2), a current position of the mobile medical imaging system is determined using signals determined by the at least one positioning sensor in a second mode at a second spatial resolution, which differs from the first spatial resolution, if the current distance between the mobile medical imaging system and the at least one object is smaller than the predetermined threshold.

In one embodiment, two or more transmitters on an operating table and three or more, preferably four transmitters on a particular imaging system are used to account for three degrees of freedom. Since the two transmitters on the operating table provide information for another three degrees of freedom, this embodiment accounts for six degrees of freedom.

In other embodiments other configurations, such as two receivers on an operating table and four transmitters on an imaging system, or four transmitters on the operating table and two sensors on the imaging system, or four receivers on the operating table and two transmitters on the imaging system are possible. By using one of these configurations, coordinates of a particular imaging system with respect to an operating table can be calculated in six degrees of freedom at the time of imaging and then, for conveyance of a surgeon, the imaging system could be moved away from the operating table. During repositioning of the imaging system, the surgeon is guided by breaking down a distance between the imaging system and the operating table into components aligned to a movement axis of the imaging system.

In another exemplary embodiment of the present invention, a computer program, which may be executed by a processor, or a computer program element is provided, that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method 200 as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A positioning arrangement for a mobile medical imaging system,
the positioning arrangement comprising:
at least one first positioning sensor configured to operate at a first spatial resolution,
at least one second positioning sensor configured to operate at a second spatial resolution that is higher than the first spatial resolution, the at least one second positioning sensor being neither a source nor a detector of the mobile medical imaging system, and
a processor configured to determine a current distance between a mobile structure of the mobile medical imaging system and at least one object in an environment of the mobile medical imaging system by using a time-difference-of-arrival and/or a time-of-flight algorithm;
wherein, in a first mode, if the current distance is greater than a predetermined threshold, the processor is configured to determine the current distance using the at least one first positioning sensor and, in a second mode, if the current distance is smaller than the predetermined threshold, the processor is configured to determine the current distance using the at least one second positioning sensor.

2. The positioning arrangement according to claim 1, wherein the at least one first positioning sensor is an ultrawideband sensor.

3. The positioning arrangement according to claim 1, wherein the at least one second positioning sensor is an ultrasound sensor.

4. A mobile medical imaging system comprising:
a mobile structure for holding an imaging device; and
the positioning arrangement according to claim 1.

5. The mobile medical imaging system according to claim 4, wherein the at least one first positioning sensor and/or the at least one second positioning sensor is attached to the mobile structure.

6. The mobile medical imaging system according to claim 4, wherein the positioning arrangement comprises:
an output device,
a memory, and
the processor;
wherein the processor is configured: to determine a position of the mobile medical imaging system at a first instant; and to store the position determined at the first instant in the memory; and to output instructions for moving the mobile structure to the position stored in the memory via the output device at a second instant.

7. The mobile medical imaging system according to claim 4, wherein the positioning arrangement is configured to detect an obstacle between a current position of the mobile medical imaging system and the at least one object.

8. The mobile medical imaging system according to claim 4, wherein the at least one first positioning sensor and/or the at least one second positioning sensor comprises at least one transmitter-receiver pair configured to determine a current position of the mobile medical imaging system relative to the at least one object.

9. The mobile medical imaging system according to claim 4, wherein the mobile structure is a C-arm holding an X-ray imaging device.

10. A method for positioning a mobile medical imaging system, the method comprising:
determining a current distance between a mobile structure and at least one object in an environment of the mobile medical imaging system by using a positioning arrangement comprising at least one first positioning sensor and at least one second positioning sensor using a time-difference-of-arrival and/or a time-of-flight algorithm;
in a first mode, if the current distance between the mobile medical imaging system and the at least one object is greater than a predetermined threshold, determining a current position of the mobile medical imaging system using signals determined by the at least one first positioning sensor at a first spatial resolution; and
in a second mode, if the current distance between the mobile medical imaging system and the at least one object is smaller than the predetermined threshold, determining a current position of the mobile medical imaging system using signals determined by the at least one second positioning sensor at a second spatial resolution, which is higher than the first spatial resolution, wherein the at least one second positioning sensor is neither a source nor a detector of the mobile medical imaging system.

11. A non-transitory computer-readable storage medium having stored a computer program comprising instructions to control a positioning arrangement for a mobile medical imaging system, the instructions, when executed by a processor, causes the processor to:
determine a current distance between a mobile structure and at least one object in an environment of the mobile medical imaging system by using a positioning arrangement comprising at least one first positioning sensor and at least one second positioning sensor using a time-difference-of-arrival and/or a time-of-flight algorithm;
in a first mode, if the current distance between the mobile medical imaging system and the at least one object is greater than a predetermined threshold, determine a current position of the mobile medical imaging system using signals determined by the at least one first positioning sensor at a first spatial resolution; and
in a second mode, if the current distance between the mobile medical imaging system and the at least one object is smaller than the predetermined threshold, determine a current position of the mobile medical imaging system using signals determined by the at least one second positioning sensor at a second spatial resolution, which is higher than the first spatial resolution, wherein the at least one second positioning sensor is neither a source nor a detector of the mobile medical imaging system.

* * * * *